United States Patent [19]

Wittmeyer

[11] Patent Number: 5,259,834

[45] Date of Patent: Nov. 9, 1993

[54] DROP FOOT BRACE WITH LATERAL SUPPORT

[76] Inventor: Frederick L. Wittmeyer, 4757 Shepherd Creek Rd., Cincinnati, Ohio 45223

[21] Appl. No.: 806,241

[22] Filed: Dec. 13, 1991

[51] Int. Cl.⁵ .............................................. A61F 3/00
[52] U.S. Cl. .................................. 602/26; 602/27
[58] Field of Search .................... 602/27, 28, 29; 128/80 E, 80 H; 36/92, 7.1 A, 173

[56] References Cited

U.S. PATENT DOCUMENTS 3,986,501 10/1976 Schad ............................ 602/28

*Primary Examiner*—Richard J. Apley
*Assistant Examiner*—Beverly A. Meindl
*Attorney, Agent, or Firm*—Steven J. Rosen

[57] ABSTRACT

The present invention provides a preformed, light weight, drop foot brace that lifts a foot by exerting a forward force on the heel to pivot the foot upwards about the ankle so that the foot won't drop during walking. The brace is also constructed so as to be light weight, easy to put on and remove and can be comfortably worn inside a shoe or without a show and still provide good lateral support by not covering the underside contact points of the foot. The brace has a shell that generally conforms to the posterior calf and is made of a resilient material that can be curved to provide the means to urge the back of the heel forward.

7 Claims, 1 Drawing Sheet

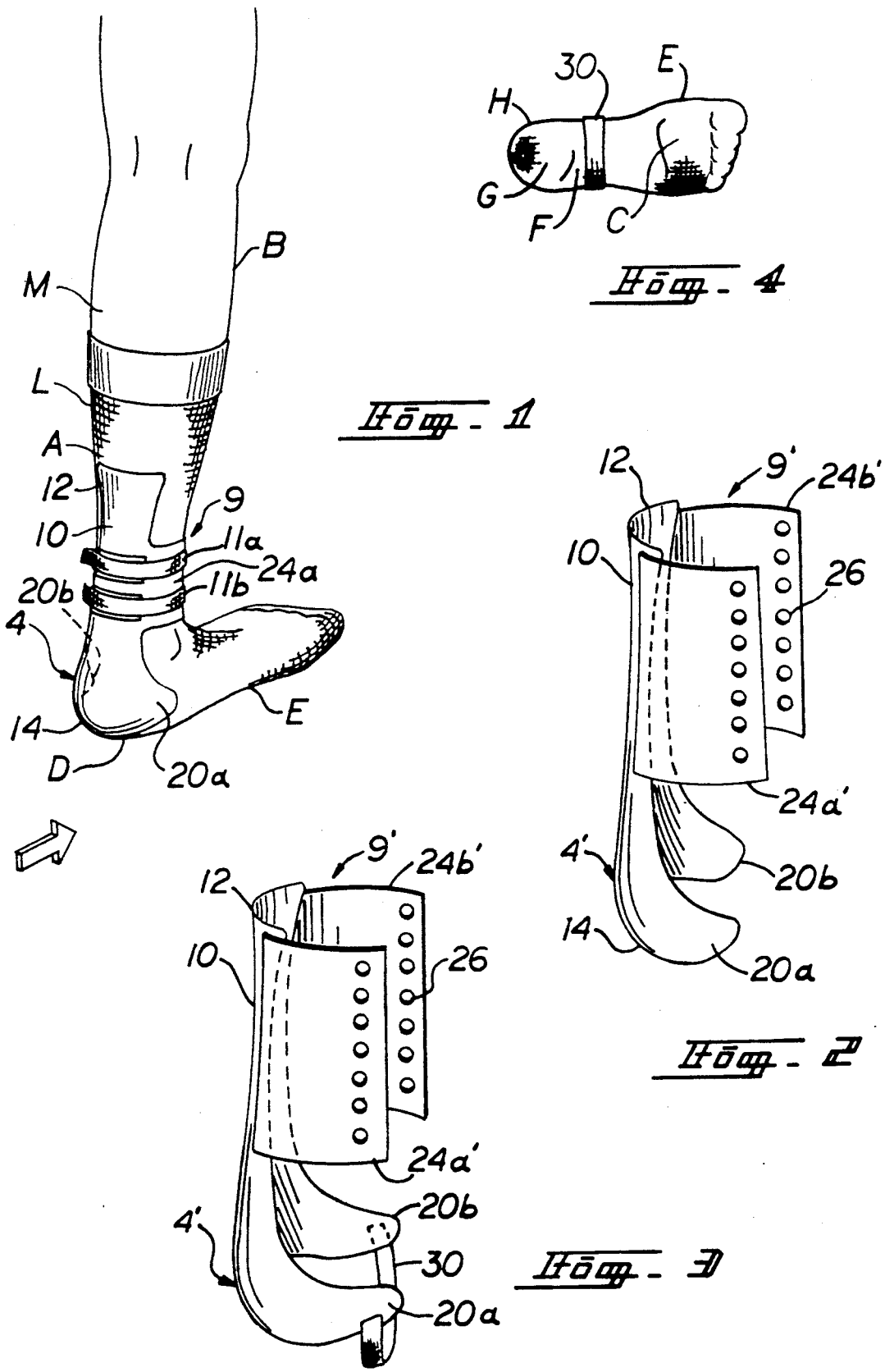

DROP FOOT BRACE WITH LATERAL SUPPORT

BACKGROUND OF THE INVENTION

1. Field of the Invention

Preformed drop foot brace having no bottom so that bottom of foot may provide stability and forward and lateral support.

2. Description of Related Art

A person who has suffered a stroke or other physical disability may lose the control of his feet such that they tend to drop down in a depending position from the legs when unsupported. This condition is particularly bothersome and may be dangerous to ambulatory people with this condition when they walk.

Various types of braces have been devised and used in the past to prevent the dropping of a foot for people with such a condition. However, such braces have had certain operational disadvantages relating to their construction and were clumsy, bulky in appearance, unyielding in structure and therefore uncomfortable, and in some instances could only be used in combination with specially designed or modified shoes. To avoid such problems and overcome the disadvantages of such braces preformed, light weight, drop foot braces that are self-conforming and removably positionable adjacent to the posterior calf portion, the heel, and instep of the leg of a wearer were developed such as the one is disclosed in U.S. Pat. No. 3,916,886, entitled "Preformed Self-Conforming Drop Foot Brace" by John E. Rogers, and which issued Nov. 4, 1975.

The problem with such braces, including the type disclosed in the Roger's patent, is that they all have a portion covering the bottom of the foot to support the foot but which prevents the foot from helping to provide lateral support and therefore the foot tends to slide particularly when inside a shoe or in contact with even only slightly slippery surfaces including carpets and wooden floors. Prior art braces effectively prevent the individual from using the ball and heel of the foot to help provide lateral frictional support, stability, and balance. The bottom portion also can cause discomfort and irritation between the foot and the forward edge of the foot supporting portion of the brace when the brace is used within a shoe.

SUMMARY OF THE INVENTION

The present invention provides a brace which lifts a foot by exerting a forward force on the heel which is gentle but sufficiently firm enough to pivot the foot upwards about the ankle so that the foot won't drop during walking. The brace is also constructed so as to be light weight, easy to put on and remove and can be comfortably worn inside a shoe and still provide good lateral support.

The present invention provides a brace having a shell that is adapted to be adjacently disposed to the posterior of the leg of the wearer and extends from below mid-calf to a position near the bottom of the foot of the leg, a means to urge the heel forward sufficiently enough to lift the foot up during walking, and a means to removably secure the shell in an adjacently disposed position relative to the calf.

The shell is preferably formed from a resilient material preferably a polymerized resin such as polypropylene or the like in sheet form. The resilient material together with a curve in the shape of the shell provides the means to push the heel forward. The preferred embodiment of the present invention also provides firm and pliable securing members attached to the sides of the shell made of a pliable shape stable material such as leather and adapted to use laces or alternatively some other securing means such as velcro straps to removably secure the shell to the leg below the calf just above the ankle.

The shell is sufficiently rigid so as to maintain it in an upwardly extending position adjacent the posterior leg of the wearer and includes a shape which urges its bottom end against the back of the heel sufficiently enough to lift the foot up during walking.

An alternative embodiment provides a shell having a forward extensions above the bottom of the foot and a strap depending from the extensions and adapted to supportably extend around the bottom of the foot thereby lifting the foot while not covering the bottom of the ball and heel of the foot.

The brace of the present invention supports the foot substantially without covering the contact surfaces of the foot thereby providing superior lateral support of the leg and balance for the wearers body. The brace may effectively be worn without a shoe unlike many of the conventional braces employing plastic shells. The brace of the present invention is light in weight, relatively inexpensive and easy to manufacture, cosmetically and aesthetically pleasing, compact, inconspicuous when worn, and easy to put on and remove.

BRIEF DESCRIPTION OF THE DRAWINGS

The foregoing aspects and other features of the invention are explained in the following description, taken in connection with the accompanying drawings where:

FIG. 1 is a perspective view of the drop foot brace removably secured to the lower leg portion of a wearer in accordance with one embodiment of the present invention.

FIG. 2 is a perspective view of the brace in FIG. 1 having leather securing bands in accordance with the preferred embodiment of the present invention.

FIG. 3 is a perspective view of the brace in FIG. 1 having an underside foot support band in accordance with another embodiment of the present invention.

DETAILED DESCRIPTION OF THE INVENTION

Illustrated in FIG. 1 is a drop foot brace 4 removably secured to the posterior side A of the leg B of a wearer's leg B. Brace 4 includes a shell 10 having a length extending from below mid-calf M of leg B to near the bottom of heel D and is removably mounted and held in position by a fastening means 9 which is positioned to be fastened around the leg below the calf L and just above the ankle K. Fastening means 9 of the embodiment shown in FIG. 1 includes a right hand shell extension members 24a and a left hand extension member (not shown but similar to 24b' of FIGS. 2 and 3) which are surrounded by velcro fastened elastic strips 11a and 11b. A more preferable fastening means is illustrated in FIG. 2 as disclosed later herein.

Shell 10 has an upper end portion 12 and lower end portion 14 that engages the heel D of foot E of leg B. Shell 10 is shaped to substantially conform to the posterior side of leg B and is curved so as provided a means to push or urge forward, in the direction of the arrow in FIG. 1, the back of heel D so as to lift and support foot E substantially perpendicular to leg B so that it won't droop during walking. Shell 10 is also sufficiently resilient so as to provide a spring like means to urge heel D forward.

Shell 10 has side extensions 20a and 20b which engage the sides of heel D and help position shell 10 and hold straight foot E. An alternative embodiment shown in FIG. 3 employ side extensions 20a and 20b to support foot E by a preferably elastic underside strap 30 removably attached to the side extensions. Underside strap 30 may be used instead of or in addition to a means for pushing forward the back of heel D as by using a curved shape of shell 10. Referring briefly to FIG. 4, underside strap 30 provides a means to pivot the foot E up and still leave the contact points of the underside F of foot E, the bottom G of heel D and ball H, exposed for providing lateral support for the leg.

FIG. 2 illustrates the preferred embodiment of the present invention wherein brace 4' includes a fastening means 9' that has firm and pliable securing members 24a' and 24b' attached to the sides of shell 10 and are made of a pliable shape stable material, preferably leather and are adapted to use laces (not shown) disposed in an interlaced fashion through lace holes 26 or alternatively some other securing means such as velcro straps to removably secure shell 10 to leg B by tying the securing members together.

Shell 10 is preferably formed from a sheet of polymerized resin, such as polypropylene, polyethylene or the like, by heating the sheet and then stretching and forming it over a suitable mold conforming to a mold of the leg and suitably curved to urge heel D forward. Methods for forming a suitable shell in accordance with the present invention are well known in the field of foot orthosis.

While the preferred and an alternate embodiment of my invention has been described fully in order to explain its principles, it is understood that various modifications or alterations may be made to the preferred embodiment without departing from the scope of the invention as set forth in the appended claims.

We claim:

1. A brace for supporting a foot subject to foot drop and which is attached to the leg for support, said brace comprising:
   a shell having a length extending from below mid-calf of the leg and terminating at the back of and near the bottom of the heel,
   a fastening means for removably securing said shell in an abutting position relative to the exterior surface of the back of the leg,
   said fastening means disposed on said shell in a position operable to fasten around the leg just above the ankle and below the calf of the leg, and
   said shell having a means to push forward the back of heel so as to lift and support the foot substantially perpendicular to leg so that it won't droop during walking.

2. A brace as claimed in claim 1 wherein said means to push forward the back of heel comprises a curve in the shape of said shell and said shell being made of a resilient material.

3. A brace as claimed in claim 2 wherein said fastening means comprises two securing members attached corresponding sides of said shell and are made of a pliable shape stable material and include a securing means to removably tie said securing members together.

4. A brace for supporting a foot subject to foot drop and which is attached to the calf of the leg for support, said brace comprising:
   a shell made of a light weight plastic sheet having a length extending from below mid-calf of the leg and terminating at the back of and near the bottom of the heel,
   a fastening means for removably securing said shell in an abutting position relative to the exterior surface of the back of the leg,
   said fastening means disposed on said shell in a position operable to fasten around the leg just above the ankle and below the calf of the leg, and
   a means to pivot the foot up so as to lift and support the foot substantially perpendicular to leg so that it won't droop during walking, said pivoting means not having a bottom that would cover the heel or ball of the foot.

5. A brace as claimed in claim 4 wherein said pivoting means comprises side extensions of said shell extending from sides of said shell and a strap depending from and extending between said side extensions and effective to fit under and support the foot.

6. A brace as claimed in claim 4 wherein said pivoting means comprises a means to push forward the back of heel so as to lift and support the foot substantially perpendicular to leg so that it won't droop during walking.

7. A brace as claimed in claim 6 wherein said means to push forward the back of heel comprises said fastening means and a curve in a shape of said shell from an upper end portion to a lower end portion of said shell and curved so as to exert a spring force to push forward on the back of the heel and said shell being made of a resilient material.

* * * * *